(12) United States Patent
Shaltry et al.

(10) Patent No.: US 11,635,404 B2
(45) Date of Patent: Apr. 25, 2023

(54) METHODS FOR MANUFACTURING ELECTROCHEMICAL SENSORS, AND RELATED ELECTROCHEMICAL SENSORS

(71) Applicant: Battelle Energy Alliance, LLC, Idaho Falls, ID (US)

(72) Inventors: Michael R. Shaltry, Idaho Falls, ID (US); Prabhat K. Tripathy, Idaho Falls, ID (US); David Estrada, Boise, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 370 days.

(21) Appl. No.: 16/840,102

(22) Filed: Apr. 3, 2020

(65) Prior Publication Data

US 2020/0355640 A1 Nov. 12, 2020

Related U.S. Application Data

(60) Provisional application No. 62/829,416, filed on Apr. 4, 2019.

(51) Int. Cl.
*G01N 27/403* (2006.01)
*G01N 27/327* (2006.01)
(Continued)

(52) U.S. Cl.
CPC ......... *G01N 27/3272* (2013.01); *G01N 27/30* (2013.01); *G01N 27/403* (2013.01); *G01N 33/205* (2019.01)

(58) Field of Classification Search
CPC .. G01N 27/3272; G01N 27/403; G01N 27/30; G01N 33/205
See application file for complete search history.

(56) References Cited

U.S. PATENT DOCUMENTS 4,052,286 A * 10/1977 Gray ..................... G01N 27/30
204/405
5,131,999 A * 7/1992 Gunasingham ........ G01N 27/38
204/402

(Continued)

FOREIGN PATENT DOCUMENTS

EP 2962995 A1 1/2016
EP 3279960 A1 2/2018

(Continued)

OTHER PUBLICATIONS

Taylor et al., "Inkjet printing of carbon supported 3-D catalyst layers for use in fuel cells," Journal for Power Source 171 (2007) 101-106 (Year: 2007).*

(Continued)

*Primary Examiner* — Alexander S Noguerola
(74) *Attorney, Agent, or Firm* — TraskBritt (57) ABSTRACT

Methods for manufacturing an electrochemical sensor include forming at least one electrode by printing at least one conductive ink on a surface of at least one substrate. The conductive ink may comprise, e.g., a platinum-group metal, another transition-group metal with a high-temperature melting point, a conductive ceramic material, glass-like carbon, or a combination thereof. The electrochemical sensor may be free of another material over the at least one electrode. An electrochemical sensor, formed according to such methods, may be configured for use in harsh environments (e.g., a molten salt environment). Electrodes of the electrochemical sensor comprise conductive material formed from a printed, conductive ink. In some embodiments, at least a portion of the electrochemical sensor is free of silver, gold, copper, silicon, and polymer materials, such portion being that which is to be exposed to the harsh environment during use of the electrochemical sensor.

21 Claims, 4 Drawing Sheets

(51) Int. Cl.
*G01N 27/30* (2006.01)
*G01N 33/205* (2019.01)

(56) References Cited

U.S. PATENT DOCUMENTS

| | | |
|---|---|---|
| 5,643,429 A | 7/1997 | Wachsman |
| 8,974,657 B2 | 3/2015 | Swartz et al. |
| 9,213,013 B2 | 12/2015 | Zevenbergen et al. |
| 10,290,432 B1 | 5/2019 | Li et al. |
| 10,431,393 B2 | 10/2019 | Bag et al. |
| 10,502,705 B2 | 12/2019 | Stowell et al. |
| 2004/0214070 A1 | 10/2004 | Simner et al. |
| 2005/0229676 A1 | 10/2005 | Moseley |
| 2009/0297923 A1 | 12/2009 | Backhaus-Ricoult et al. |
| 2010/0143818 A1 | 6/2010 | Rieke et al. |
| 2011/0108439 A1 | 5/2011 | Gourishankar et al. |
| 2017/0095187 A1* | 4/2017 | Svoboda .......... A61B 5/150755 |
| 2018/0059044 A1* | 3/2018 | Berduque .......... G01N 27/4045 |
| 2019/0062581 A1 | 2/2019 | Zhang |

FOREIGN PATENT DOCUMENTS

| | | |
|---|---|---|
| GB | 2426343 B | 11/2006 |
| WO | 2008/009951 A1 | 1/2008 |
| WO | WO 2104053855 A1 * | 4/2014 ............. G01N 27/50 |

OTHER PUBLICATIONS

Vargas-García et al., "Pt Electrode-Based Sensor Prepared by Metal Organic Chemical Vapor Deposition for Oxygen Activity Measurement in Glass Melts," Sensors and Materials, vol. 14, No. 1 (2002) 047-056 (Year: 2002).*

* cited by examiner

METHODS FOR MANUFACTURING
ELECTROCHEMICAL SENSORS, AND
RELATED ELECTROCHEMICAL SENSORS

CROSS-REFERENCE TO RELATED
APPLICATION

This application claims the benefit, under 35 U.S.C. § 119(e), of U.S. Provisional Patent Application Ser. No. 62/829,416, filed Apr. 4, 2019, the disclosure of which is hereby incorporated herein in its entirety by this reference.

STATEMENT REGARDING FEDERALLY
SPONSORED RESEARCH OR DEVELOPMENT

This invention was made with government support under Contract No. DE-AC07-05-ID14517 awarded by the United States Department of Energy. The government has certain rights in the invention.

TECHNICAL FIELD

Embodiments of the disclosure relate generally to electrochemical sensors and to methods for forming the electrochemical sensors. More particularly, embodiments of the disclosure relate to methods for manufacturing electrochemical sensors configured for use in harsh environments. Related electrochemical sensors are also disclosed.

BACKGROUND

Electrochemical sensors have been in use in industry for many decades. For example, electrochemical sensors may be used to take various electrochemical measurements within a system to evaluate the properties of materials within that system, such as to evaluate the properties of a solvent or other chemicals within the system. Fundamental electrochemical measurements frequently use a three-electrode setup. The three electrodes generally include a "working" electrode, a "counter" electrode, and a "reference" electrode.

Often, conventional electrochemical sensors are ill suited for use in harsh environments, such as high-temperature environments, corrosive environments, oxidizing environments, reducing environments, radioactive environments, or the like. One particular category of harsh environments in which most conventional electrochemical sensors are ill suited is the category of molten salt environments, e.g., systems with molten-salt-based solvents, which are generally high-temperature and corrosive environments and may also be oxidizing and radioactive. Designing and fabricating sensors conducive for taking accurate measurements within such harsh environments continue to present challenges.

BRIEF SUMMARY

In some embodiments, disclosed is a method for manufacturing an electrochemical sensor. The method comprises forming at least one electrode on at least one substrate. Forming the at least one electrode comprises printing at least one conductive ink on a surface of the at least one substrate. The conductive ink comprises one or more of a platinum-group metal, another transition-group metal with a melting point greater than about 400° C., a conductive ceramic material, vitreous carbon, or a combination of any of the foregoing. The electrochemical sensor is free of another material over the at least one electrode.

In some embodiments, an electrochemical sensor, for use in a molten salt environment, comprises a working electrode on at least one substrate. The working electrode comprises a conductive material. A counter electrode is also on the at least one substrate. The counter electrode comprises another conductive material. At least a portion of the electrochemical sensor—i.e., the portion that is to be inserted into a molten salt environment during use of the electrochemical sensor—is free of silver, gold, copper, silicon, and polymer materials.

In some embodiments, a microelectrochemical sensor, for use in a molten salt environment, comprises a first electrode printed on a surface of a substrate. The first electrode comprises a conductive oxide material. A second electrode is printed on a surface of the substrate. The second electrode comprising another conductive oxide material.

DETAILED DESCRIPTION

Sensors manufactured according to embodiments of methods of the disclosure may be configured for use in harsh environments (e.g., high-temperature environments, high-pressure environments, corrosive environments, oxidizing environments, reducing environments, environments with other obnoxious gases, radioactive environments), such as molten salt environments (e.g., systems with molten-salt-based solvents). That is, the methods of fabrication facilitate careful control of the structures and relative spatial dispositions, even at small sizes, of manufactured apparatus features. Therefore, the methods enable forming electrochemical sensors (e.g., microsensors) that include intricate features (e.g., electrodes) and/or complex geometries. Accordingly, the formed electrochemical sensors may be configured to accurately take measurements, e.g., in harsh environments, such as measurements that are not limited by diffusion characteristics. Such sensors may, therefore, provide improved accuracy in voltage and/or current measurements in, e.g., molten salt environments or other harsh environments.

As used herein, the term "micro," when used to describe a sensor (e.g., an electrochemical sensor), means and refers to the sensor having a maximum dimension—of its outermost horizontal and vertical dimensions of a substrate—that is less than 1,000 µm, e.g., less than 750 µm, e.g., less than 500 µm.

As used herein, the term "macro," when used to describe a sensor (e.g., an electrochemical sensor), means and refers to the sensor having a maximum dimension—of its outermost horizontal and vertical dimensions of a substrate—that is greater than or equal to 1,000 µm.

As used herein, the term "molten salt" refers to molten media, which may or may not be wholly ionic or derived from simple salts.

As used herein, the terms "molten salt environment" and "molten salt system" refer to an environment or a system that includes one or more molten salts, e.g., as a solvent.

As used herein, the terms "high temperature" and "high-temperature" each refer to a temperature greater than or equal to about 400° C., such as temperatures greater than or equal to about 500° C., e.g., greater than or equal to about 600° C., e.g., greater than or equal to about 700° C.

As used herein, the term "fixed," e.g., as when used in association with the relative spatial positioning or arrangement of structures, means and includes the structures being configured and/or disposed such that they cannot be physically moved, relative to one another—either nearer to or father away from one another—without a substantial structural degradation to either one of the structures, themselves, or to a supportive structure.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof.

As used herein, the term "may," when used with respect to a material, structure, feature, or method act, indicates that such is contemplated for use in implementation of an embodiment of the disclosure, and such term is used in preference to the more restrictive term "is" so as to avoid any implication that other compatible materials, structures, features, and methods usable in combination therewith should or must be excluded.

As used herein, the term "configured" refers to a size, shape, material composition, and arrangement of one or more of at least one structure and at least one apparatus facilitating operation of one or more of the structure and the apparatus in a predetermined way.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, even at least 99.9% met, or even 100.0% met.

As used herein, the terms "about" or "approximately," when used in reference to a numerical value for a particular parameter, are inclusive of the numerical value and a degree of variance from the numerical value that one of ordinary skill in the art would understand is within acceptable tolerances for the particular parameter. For example, "about" or "approximately," in reference to a numerical value, may include additional numerical values within a range of from 90.0% to 110.0% of the numerical value, such as within a range of from 95.0% to 105.0% of the numerical value, within a range of from 97.5% to 102.5% of the numerical value, within a range of from 99.0% to 101.0% of the numerical value, within a range of from 99.5% to 100.5% of the numerical value, or within a range of from 99.9% to 100.1% of the numerical value.

As used herein, the term "and/or" includes any and all combinations of one or more of the associated listed items.

Methods for manufacturing electrochemical sensors, according to embodiments of the disclosure, include use of advanced manufacturing (e.g., additive manufacturing) techniques to form at least the electrodes of the sensors. Additive manufacturing may be otherwise known in the art as "three-dimensional printing" or "3D printing."

While additive manufacturing has been used to form other structures (e.g., plastic toys, concrete walls, organic tissue), the methods of this disclosure, unexpectedly, make use of advanced manufacturing (e.g., additive manufacturing) techniques to print conductive inks onto at least one substrate to fabricate sensors configured for use in harsh environments (e.g., molten salt environments). In contrast, as a hypothetical example, additive manufacturing to form sensors with, e.g., polymer coatings formed on silicon chip substrates, may be suitable to form such sensors for use in non-harsh environments, but the materials or structures of such sensors may inevitably degrade (e.g., delaminate) and be ineffective in harsh environments.

Figure 1:
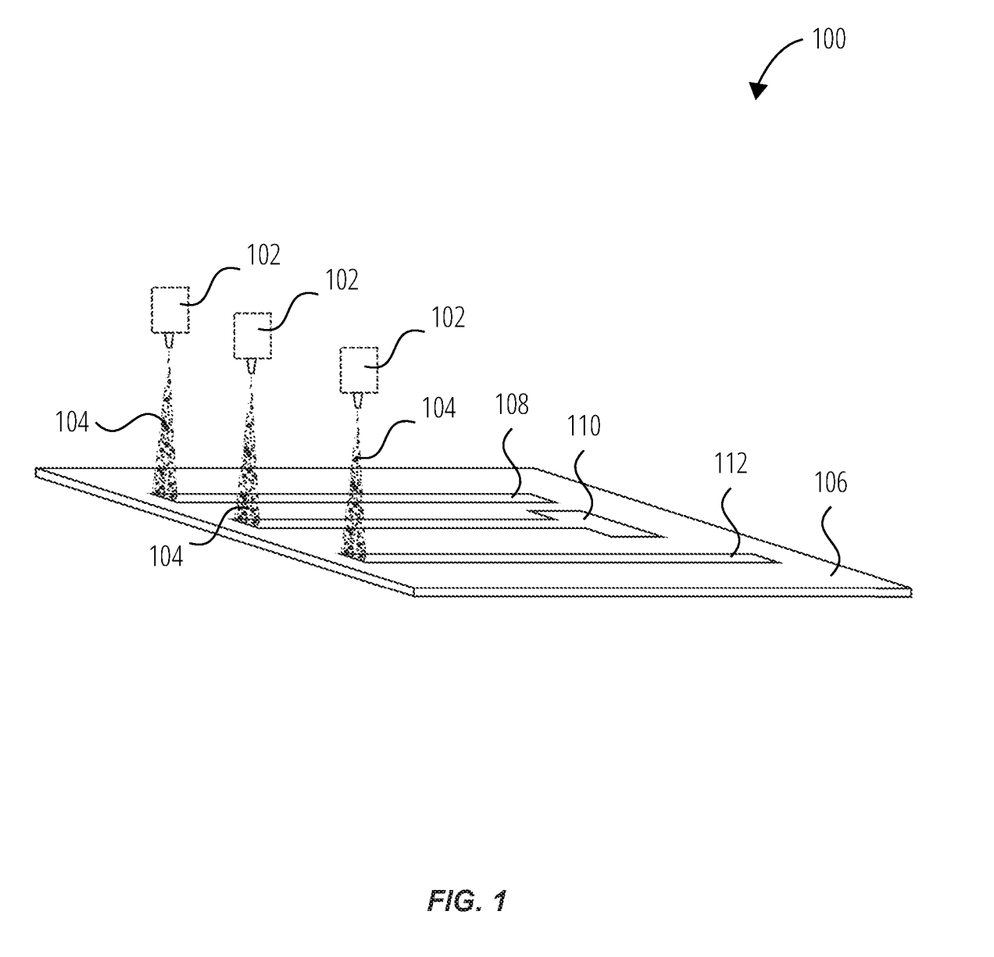
FIG. 1 is a schematic illustration of a stage of a method for manufacturing an electrochemical sensor, according to embodiments of the disclosure, the stage including printing at least one electrode on at least one substrate of the electrochemical sensor.

With reference to FIG. 1, additive manufacturing techniques may be used to form at least one electrode on at least one substrate of an electrochemical sensor. The additive manufacturing includes a printing stage 100 in which one or more print head 102 (e.g., of an aerosol jet printer, of an inkjet printer, of a plasma jet printer, of a microdispenser printing system) prints ink 104 onto at least one substrate 106 to form one or more electrodes (e.g., a working electrode 108, a counter electrode 110, a reference electrode 112). Accordingly, the conductive features (e.g., electrodes, such as the working electrode 108, the counter electrode 110, the reference electrode 112), formed by printing according to embodiments of the disclosure, may comprise, consist essentially of, or consist of any one or more of the conductive materials described above with regard to the composition of the ink 104.

In some embodiments, after the initial printing, the ink 104 may be subjected to drying and/or setting acts to finalize the ink 104 in the form of the at least one electrode. Such drying and/or setting acts may include various thermal, chemical, and/or photonic sintering techniques.

The at least one substrate 106 may be formed of material(s) that are formulated and/or structured to withstand the expected harsh conditions. For example, the substrate 106 (or, substrates, in other embodiments) may comprise, consist essentially of, or consist of a ceramic material (e.g., ceramic material(s) resistant to corrosion, such as aluminum oxide ($Al_2O_3$), magnesium oxide (MgO), boron nitride (BN), or combinations of any one or more thereof). In some embodiments, the substrate 106 (or substrates) may comprise, consist essentially of, or consist of sapphire, quartz, or combinations thereof.

In some embodiments, the material(s) printed on the substrate 106 (or substrates)—i.e., the "ink" (ink 104)—to form the electrodes (e.g., the working electrode 108, the counter electrode 110, the reference electrode 112) may comprise, consist essentially of, or consist of one or more conductive materials resistant to corrosion, such as (i) one or more platinum-group metal (i.e., iridium (Ir), ruthenium (Ru), rhodium (Rh), platinum (Pt), osmium (Os), palladium (Pd)), (ii) one or more other transition-group metal with a high-temperature melting point (e.g., nickel (Ni), titanium (Ti), zirconium (Zr), tungsten (W)), (iii) one or more alloys of platinum-group metals, (iv) one or more alloys of one or more platinum-group metal with one or more other transition-group metal (e.g., alloys of one or more platinum-group metal (such as any one or more of the previously listed example platinum-group metals) with one or more of nickel (Ni), titanium (Ti), zirconium (Zr), tungsten (W), chromium (Cr), copper (Cu), molybdenum (Mo), niobium (Nb), hafnium (Hf), tantalum (Ta), rhenium (Re)), (v) one or more conductive ceramic material(s) (e.g., conducting-oxide-based material(s), such as conducting-oxide-based materials having a perovskite crystal structure (e.g., $CaTiO_3$, $Li_2PtO_3$, $Li_2IrO_3$, $Li_2RuO_3$, $CaPtO_3$, $CaIrO_3$, $CaRuO_3$)), (vi) glass-like carbon (also referred to in the art as "vitreous carbon"), and/or (vii) any other combination of one or more of the foregoing. Such inks 104 used in the method may be commercially available inks comprising one or more of the aforementioned conductive materials or may be custom formulated to include one or more of the aforementioned conductive materials. The inks 104 may be in a flowable form, such as in flowable particle form, liquid solution form, or molten form. As printed using the inks 104, the electrodes (e.g., the working electrode 108, the counter electrode 110, the reference electrode 112) of the electrochemical sensor(s) may withstand harsh environments, and the fabricated electrochemical sensor(s) may, therefore, be configured for use in harsh environments, such as molten salt systems.

To fabricate an electrochemical sensor by additive manufacturing (e.g., printing), as in the printing stage 100 of FIG. 1, each of the electrodes of the sensor (e.g., each of the working electrode 108, the counter electrode 110, the reference electrode 112) may be printed independently, in any order, using one or more of the print heads 102, on an associated surface of the one or more substrates 106. Alternatively, one or more of the print heads 102 may be used to print all of the electrodes (e.g., the working electrode 108, the counter electrode 110, and the reference electrode 112) concurrently. In embodiments in which multiple print heads 102 are used, each of the print heads 102 may be connected to a separate reservoir of the ink 104, formulated according to the respective one or more of the electrodes (e.g., the working electrode 108, the counter electrode 110, the reference electrode 112) to be printed by each print head 102. In embodiments in which a single print head 102 is used and the electrodes (e.g., the working electrode 108, the counter electrode 110, the reference electrode 112) include more than one conductive material, the print head 102 may be in communication with multiple reservoirs of different inks 104, each formulated according to the respective electrode to be printed with such ink 104.

The type of printing system (e.g., printer) and print head 102 used may be tailored according to the ink 104, such as according to the viscosity of the inks 104. To print inks of a lower viscosity (e.g., less than about 100 cP), an inkjet printer may be used. To print inks of a greater viscosity (e.g., greater than about $10^5$ cP), a microdispensing printing system may be used. To print inks of a medium viscosity (e.g., greater than about 100 cP and less than about $10^5$ cP), an aerosol jet printer may be used.

In some embodiments, the substrate 106 (or substrates) may also be first fabricated by additive manufacturing, which may facilitate control of the porosity of the substrate 106 material. In other embodiments, the substrate 106 (or substrates) may be formed by conventional methods and then used as the receiving surface during the formation (e.g., printing) of the conductive material (e.g., the ink 104) to define the electrodes.

In some embodiments, multiple electrochemical sensors may be fabricated using a single substrate (e.g., a unitary substrate, a monolithic substrate), such that multiple groups of electrodes (e.g., multiple groups of the working electrode 108, the counter electrode 110, the reference electrode 112), in the same or different configurations, in the same or different materials, respectively, may be printed on a single substrate. The single substrate may support the multiple groups of electrodes (e.g., the multiple electrochemical sensors) during use of the multiple electrochemical sensors; or, in some embodiments, after printing, the single substrate may be cut or otherwise divided into individual or sub-groups of the electrochemical sensors.

Whether fabricating (e.g., printing) the electrodes of one or more sensors on one or more substrates, forming the electrodes by printing (e.g., by inkjet printing, by aerosol jet printing) facilitates fabricating sensors, such as microsensors (e.g., microelectrochemical sensors), having electrodes (e.g., working electrode 108, counter electrode 110, reference electrode 112) in intricate patterns and/or complex geometries. In some embodiments, a width (e.g., lateral dimension) of an electrode (e.g., a narrowest point of the working electrode 108, the counter electrode 110, and/or the reference electrode 112) may be on the order of less than about 100 μm, such as between about 100 μm and about 10 μm (e.g., about 70 μm) or such as less than about 1 μm (e.g., about 100 nm), and the sensor fabricated may be a microsensor. Fabricating such micro-sized electrodes of the aforementioned materials—e.g., materials capable of withstanding harsh environments—may not be possible, or may be more difficult and expensive to achieve, using conventional fabrication methods, particularly for micro-sized electrodes with intricate patterns and complex geometries.

Being formed of printed ink 104 material (e.g., printed conductive material), the electrodes of this or other embodiments may be disposed wholly on a respective surface of the one or more substrates (e.g., the surface of the substrate 106) in one or more monolayers of the conductive ink 104 material or in multiple layers of the conductive ink 104 material. The substrates (e.g., the substrate 106 or at least the ink-receiving surface of the substrate) may be substantially planar and nonporous, in some embodiments, such that the electrodes may not extend into the substrate(s) (e.g., into the substrate 106). The ink 104 may be conformally formed (e.g., printed) on the substrate(s) (e.g., the substrate 106). In some embodiments, the ink 104 may—after drying or other setting of the ink 104 into a final material form—define electrodes that are less than about 1 mm in thickness, relative to the surface of the respective substrate (e.g., the surface of the substrate 106). In some embodiments, such as those printing the ink 104 using an inkjet printer, an aerosol jet printer, a microdispense printer, or a plasma jet printer, may deposit the ink 104 at a thickness that can be tuned between about 100 nm and about 50 μm. The properties (e.g., viscosity) of the ink 104 and the number of print passes made when printing the ink 104 may be tailored according to the desired thickness of the resulting printed feature (e.g., the electrodes). The resulting conductive features (e.g., electrodes) formed from the ink 104 may be substantially structurally stable and robust (e.g., in dimension, microstructure, and/or other physical characteristics). In some embodiments, the printed conductive features, formed from the ink 104, may be substantially nonporous (e.g., with less than about 10 vol. % void or other non-solid space).

Figure 2:
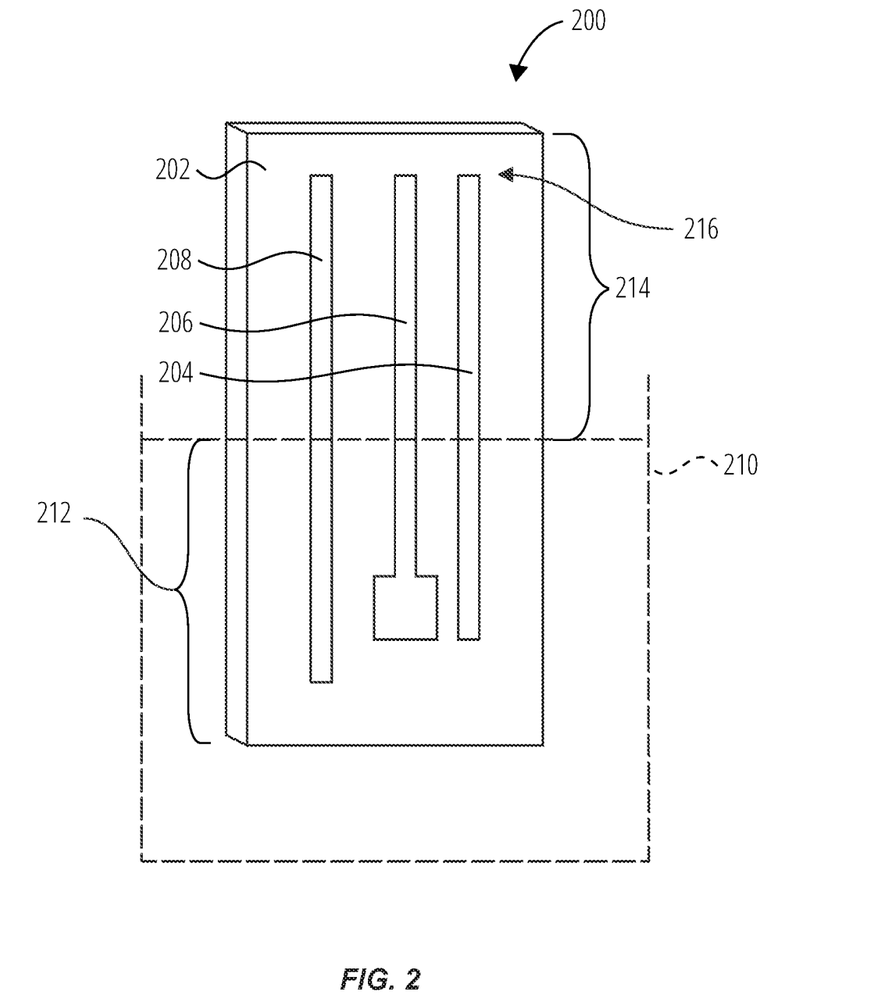
FIG. 2 is a schematic illustration of an electrochemical sensor, fabricated according to methods of the disclosure and illustrated in use within a harsh environment, according to embodiments of the disclosure, wherein the electrodes of the electrochemical sensor have been formed by printing the electrodes on a single substrate.

With reference to FIG. 2, illustrated is an electrochemical sensor 200 that may be fabricated according to the printing stage 100 of FIG. 1, though with electrodes and/or substrate(s) of different configurations. The electrochemical sensor 200 may be a microelectrochemical sensor. A substrate 202 of the electrochemical sensor 200 may comprise, consist essentially of, or consist of any one or more of the materials described above with regard to the substrate 106 of FIG. 1. Electrodes (e.g., a working electrode 204, a counter electrode 206, and a reference electrode 208) of the electrochemical sensor 200 may comprise, consist essentially of, or consist of any one or more of the materials described above with regard to the electrodes (e.g., the working electrode 108, the counter electrode 110, and the reference electrode 208) of FIG. 1. That is, the electrodes (e.g., the working electrode 204, the counter electrode 206, the reference electrode 208) may each be formed of one or more of the aforementioned conductive materials for the ink 104. In embodiments in which the ink 104 includes a solvent, the solvent may or may not be included in the finally-formed conductive features (e.g., the electrodes), though the conductive material of the ink 104 may remain—in who or in part—within the finally-formed conductive features. For example, in some embodiments, the substrate 202 of the electrochemical sensor 200 may comprise, consist essentially of, or consist of sapphire or quartz; the working electrode 204 and the counter electrode 206 may each comprise, consist essentially of, or consist of a platinum group metal or alloy (e.g., platinum or a platinum alloy); and the reference electrode 208 may comprise, consist essentially of, or consist of nickel (Ni), platinum (Pt), an alloy thereof, and/or glass-like carbon. In such embodiments, or in other embodiments, the electrochemical sensor 200 of FIG. 2 may be configured for use in a molten salt environment comprising, consisting essentially of, or comprising a mixture (e.g., a eutectic mixture) of LiCl and KCl molten salt, at temperatures of about 500° C. or greater.

The electrochemical sensor 200 may be configured for use in a harsh environment 210. In embodiments in which the harsh environment 210 includes a molten salt environment, the molten salt environment may include molten salt solvents such as, for example and without limitation, halide-based molten salts, such as chloride-based molten salts, bromide-based molten salts, fluoride-based molten salts, or mixtures (e.g., "mixed melt") thereof.

The electrochemical sensors, fabricated according to methods of the disclosure, including the electrochemical sensor 200 of FIG. 2, may be free of materials (e.g., in the electrodes, such as the working electrode 204, the counter electrode 206, and the reference electrode 208, and/or in the substrate 202) that would degrade or otherwise become ineffective in harsh environments, at least in those portions of the electrochemical sensor 200 that would come into contact with, or be in close proximity to, the harsh environments (e.g., a molten salt environment) during use of the sensor. For example, to use the electrochemical sensor 200 to take measurements within the harsh environment 210 (e.g., a molten salt environment), at least one portion 212 of the electrochemical sensor 200 may be inserted into (e.g., submerged within) the harsh environment 210. Another portion 214 of the electrochemical sensor 200 may extend out of the harsh environment 210 during use.

The electrochemical sensor 200 may be formed such that the electrodes (e.g., the working electrode 204, the counter electrode 206, the reference electrode 208)—and, e.g., the electrochemical sensor 200 overall or the portion 212 of the electrochemical sensor 200 to be submerged in the harsh environment 210—may be entirely or substantially free of metals prone to degradation (e.g., electrochemical corrosion) when exposed to a harsh environment (e.g., a corrosive environment, such as an environment with in situ generation of oxygen, chlorine, fluorine, bromine, and/or iodine), such as silver, gold, and/or copper. In these or other embodiments, the substrate 202—and, e.g., the electrochemical sensor 200 overall or the portion 212 of the electrochemical sensor 200 to be submerged in the harsh environment 210—may be free of silicon. In any of the aforementioned embodiments or in other embodiments, the electrochemical sensor 200 may be free or substantially free—e.g., overall, or in the portion 212 to be submerged in the harsh environment 210—of other materials that degrade electrochemically or physically under harsh conditions, such as being free of polymer materials and/or other materials that would tend to melt at the temperatures of the harsh conditions.

In some embodiments, such as that of FIG. 2, the electrodes (e.g., the working electrode 204, the counter electrode 206, the reference electrode 208) of the electrochemical sensor 200 may be formed (e.g., printed) on a single substrate (e.g., substrate 202). Accordingly, the electrodes (e.g., the working electrode 204, the counter electrode 206, the reference electrode 208) may be printed on a surface of the substrate 202 so that the electrodes (e.g., the working electrode 204, the counter electrode 206, the reference electrode 208) have a fixed position relative to one another. This fixed arrangement may prevent possible measurement errors that may otherwise arise—in conventional electrochemical sensors that do not include electrodes with fixed relative positions—should one or more electrode happen to be moved further away from or nearer to another electrode of the sensor. The fixed arrangement of the electrodes (e.g., the working electrode 204, the counter electrode 206, the reference electrode 208) of single-substrate electrochemical sensors (e.g., the electrochemical sensor 200) of the disclosure may also avoid possible measurement errors due to, e.g., electrode morphologies, electrode inhomogeneities, environmental vibrations, etc. Moreover, with the spatial relationship of the electrodes (e.g., the working electrode 204, the counter electrode 206, the reference electrode 208) of the electrochemical sensor 200 being fixed, the electrochemical sensor 200 may not require electrode maintenance or calibration steps, before use, to ensure the electrodes (e.g., the working electrode 204, the counter electrode 206, the reference electrode 208) are in an intended spatial relationship during use.

Electrochemical sensors, such as the electrochemical sensor 200 of FIG. 2, fabricated by printing the electrodes (e.g., the working electrode 204, the counter electrode 206, the reference electrode 208) on a single substrate (e.g., the substrate 202), may be less sensitive to external environmental factors that may otherwise detract from measurement accuracy. That is, a mechanical vibration (e.g., a physical vibration of the floor of the room) in which the sensor (e.g., electrochemical sensor 200) is being used, may not impact the measurements being taken by the sensor (e.g., the electrochemical sensor 200). The resulting data taken by using the sensor (e.g., the electrochemical sensor 200) may, therefore, be clearer and/or more accurate (e.g., have more distinctive transitions or peaks in a data plot, such as in a plot of current versus applied potential) and easier to analyze.

Accordingly, sensors such as the electrochemical sensor 200 of FIG. 2 may be configured to avoid measurement uncertainties.

To configure the electrochemical sensor 200 for use in the harsh environment 210, an AC/DC power supply unit or potentiostat may be connected to the electrodes (e.g., the working electrode 204, counter electrode 206, the reference electrode 208)—e.g., by affixed or selectively removable electrical connections to the electrodes (e.g., the working electrode 204, the counter electrode 206, the reference electrode 208) at, e.g., a distal portion 216 of each. Such electrical connects may be attached, permanently or removably, by, e.g., soldering, conductive clips, or other physical connection.

Once the electrochemical sensor 200 has been formed and connected to a power supply unit or potentiostat, the electrochemical sensor 200 may then be inserted (e.g., the portion 212 of the electrochemical sensor 200 may then be inserted) into the environment (e.g., the harsh environment 210) in which measurements are to be taken by the electrochemical sensor 200, such as measurements to record electrochemical signatures (e.g., both qualitative and quantitative) in the environment (e.g., the harsh environment 210). For example, the portion 212 of the electrochemical sensor 200 may be lowered into the harsh environment 210, e.g., a molten salt environment, to electrochemically evaluate a given solute concentration in the molten salt solvent.

Figure 3A:
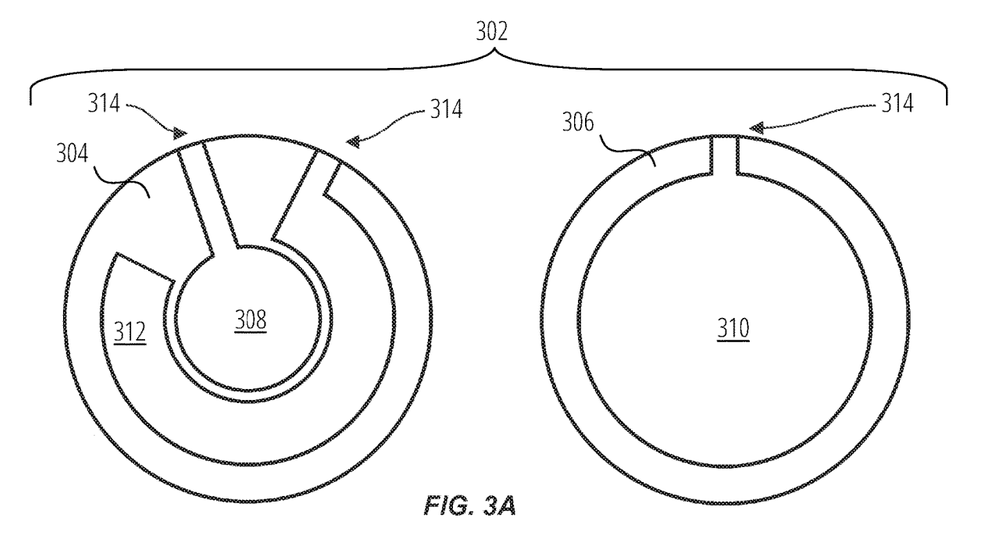
FIG. 3A is a top plan, schematic illustration of electrodes printed on first and second substrates of an electrochemical sensor, fabricated according to embodiments of the methods of the disclosure.

FIG. 3A illustrates an electrochemical sensor 302, which may be formed according to the aforementioned methods (e.g., the printing stage 100 of FIG. 1). The electrochemical sensor 302 includes a first substrate 304 and a second substrate 306, each of which may be substantially circular as defined by an outer perimeter of each. A working electrode 308 is printed on the first substrate 304 (e.g., on one surface of the first substrate 304). A counter electrode 310 is printed on the second substrate 306 (e.g., on one surface of the second substrate 306). A reference electrode 312 is printed on the first substrate 304, e.g., on the same surface of the first substrate 304 on which the working electrode 308 is printed. Therefore, at least the reference electrode 312 and the working electrode 308 are printed to be in a fixed spatial relationship to one another. Forming (e.g., printing) both the reference electrode 312 and the working electrode 308 on the same substrate (e.g., the first substrate 304) facilitates fixedly disposing the reference electrode 312 close (e.g., as close as possible) to the working electrode 308.

Each of the first substrate 304 and the second substrate 306 may comprise, consist essentially of, or consist of any one or more of the materials described above with regard to the substrate 106 of FIG. 1 and/or the substrate 202 of FIG. 2. Each of the working electrode 308, the counter electrode 310, and the reference electrode 312 may comprise, consist essentially of, or consist of any one or more of the materials described above with regard to the working electrode 108, the counter electrode 110, and the reference electrode 208, respectively, of FIG. 1 and/or the working electrode 204, the counter electrode 206, and the reference electrode 208, respectively, of FIG. 2. The electrochemical sensor 302 may be free of any one or more of the materials, described above, of which the electrochemical sensor 200 of FIG. 2 may be free.

Each of the electrodes (e.g., the working electrode 308, the counter electrode 310, the reference electrode 312) may be printed to include a distal portion 314 that extends to or proximate an edge of the respective one of the first substrate 304 and the second substrate 306. The distal portion 314 of the working electrode 308 may be proximate the distal portion 314 of the reference electrode 312 (e.g., within a same quadrant of the first substrate 304).

The reference electrode 312 may at least partially laterally circumscribe the working electrode 308. The counter electrode 310 may define an outer diameter (not including its distal portion 314) that is about as large as an outer dimeter of the reference electrode 312 (not including its distal portion 314). The counter electrode 310 may have a surface area greater than (e.g., about ten times to twenty times greater than) a surface area of the working electrode 308, e.g., to ensure the electrochemical reaction is rate limited by the working electrode 308, rather than by the counter electrode 310. In some embodiments the outer diameter of each of the substrates (e.g., the first substrate 304, the second substrate 306) may be about 10 mm or less. In other embodiments, the outer diameter of each of the substrates may be less than about 1000 μm, and a greatest lateral (e.g., radius, diameter) dimension of each of the electrodes (e.g., the working electrode 308, the counter electrode 310, the reference electrode 312) may be less than about 1000 μm.

Figure 3B:
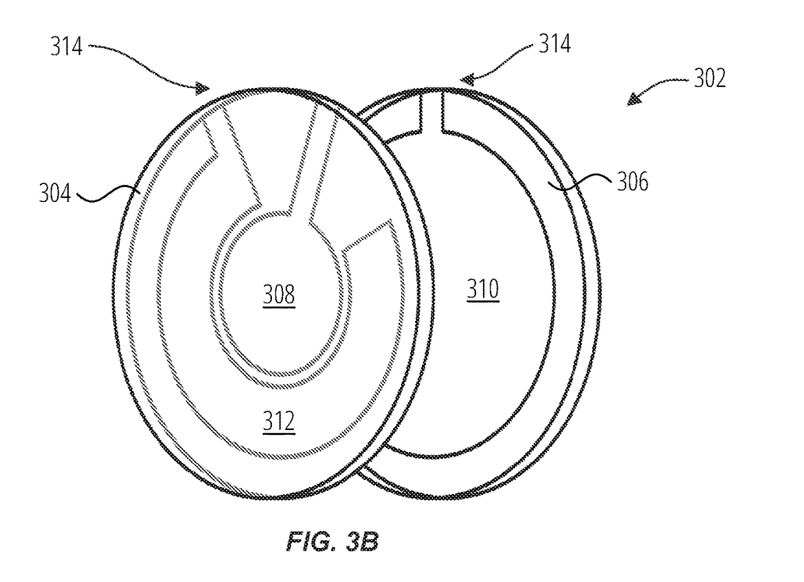
FIG. 3B is a perspective schematic illustration of the substrates and electrodes of the electrochemical sensor of FIG. 3A arranged in a spatial relationship for use within a harsh environment.

Prior to use, or at least prior to taking measurements with the electrochemical sensor 302, the first substrate 304 and the second substrate 306 may be positioned a predetermined distance from one another with the electrode-including surface of each directed toward one another. The distal portion 314 of each of the working electrode 308, the counter electrode 310, and the reference electrode 312 may be directed upward. A separate support structure may be used to hold the first substrate 304 and the second substrate 306 in a fixed spatial relationship relative to one another. In other embodiments, the first substrate 304 and the second substrate 306 may be affixedly, physically connected to one another prior to use, and, in some such embodiments, prior to printing the electrodes (e.g., the working electrode 308, the counter electrode 310, the reference electrode 312) thereon. After printing the electrodes and before or after supporting the substrates in a desired relative position, electrical leads may be connected to the distal portion 314 of each of the electrodes (e.g., the working electrode 308, the counter electrode 310, the reference electrode 312) to electrically and operatively connect the electrochemical sensor 302 to a power source and or data-acquisition system.

Figure 4A:
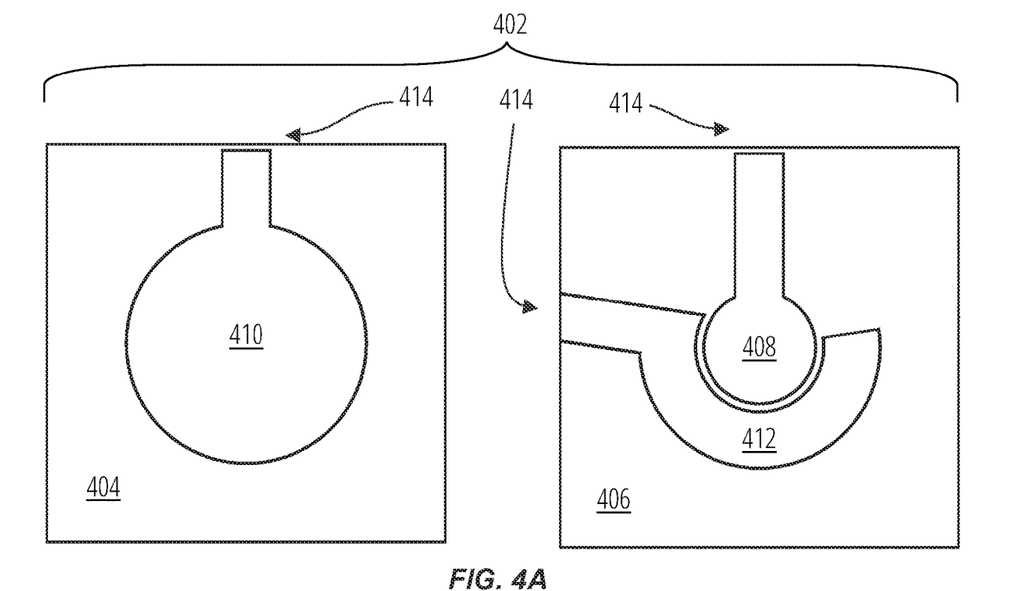
FIG. 4A is a top plan, schematic illustration of electrodes printed on first and second substrates of an electrochemical sensor, fabricated according to embodiments of the methods of the disclosure.

FIG. 4A illustrates an electrochemical sensor 402, which may be formed according to the aforementioned methods (e.g., the printing stage 100 of FIG. 1). The electrochemical sensor 402 includes a first substrate 404 and a second substrate 406. A working electrode 408 is printed on the second substrate 406 (e.g., on one surface of the second substrate 406). A counter electrode 410 is printed on the first substrate 404 (e.g., on one surface of the first substrate 404). A reference electrode 412 is printed on the second substrate 406, e.g., on the same surface of the second substrate 406 on which the working electrode 408 is printed. Therefore, at least the working electrode 408 and the reference electrode 412 are printed to be in a fixed spatial relationship to one another, which may be close (e.g., as close as possible) spatial relationship.

Each of the first substrate 404 and the second substrate 406 may comprise, consist essentially of, or consist of any one or more of the materials described above with regard to the substrate 106 of FIG. 1, the substrate 202 of FIG. 2, the first substrate 304 of FIG. 3A and FIG. 3B, and/or the second substrate 306 of FIG. 3A and FIG. 3B. Each of the working electrode 408, the counter electrode 410, and the reference electrode 412 may comprise, consist essentially of, or consist of any one or more of the materials described above with regard to the working electrode 108, the counter electrode 110, and the reference electrode 208, respectively, of FIG. 1; the working electrode 204, the counter electrode 206, and the reference electrode 208, respectively, of FIG. 2; and/or the working electrode 310, the counter electrode 308, and the reference electrode 312 of FIG. 3A and FIG. 3B. The electrochemical sensor 402 may be free of any one or more of the materials, described above, of which the electrochemical sensor 200 of FIG. 2 and/or the electrochemical sensor 302 of FIG. 3A and FIG. 3B may be free.

Each of the electrodes (e.g., the working electrode 408, the counter electrode 410, the reference electrode 412) may be printed to include a distal portion 414 that extends to or proximate an edge of the respective one of the first substrate 404 and the second substrate 406. Each of the first substrate 404 and the second substrate 406 may be rectangular in their primary surfaces. The distal portion 414 of the working electrode 408 and of the distal portion 414 of the counter electrode 410 may extend to or proximate a top edge of the second substrate 406 and the first substrate 404, respectively. The distal portion 414 of the reference electrode 412 may extend to a side edge of the second substrate 406. The reference electrode 412 may partially, laterally circumscribe the working electrode 408. The counter electrode 410 may define an outer diameter (not including its distal portion 414) that is about as large as an outer dimeter of the reference electrode 412 (not including its distal portion 414). The counter electrode 410 may have a surface area greater than (e.g., about ten times to twenty times greater than) a surface area of the working electrode 408, e.g., to ensure the electrochemical reaction is limited by the working electrode 408. In some embodiments, the greatest outer dimension (e.g., width or length) of each of the substrates (e.g., the first substrate 404, the second substrate 406) may be about 10 mm or less. In other embodiments, the greatest outer dimension of each of the substrates may be less than about 1000 µm, and a greatest lateral (e.g., radius, diameter) dimension of each of the electrodes (e.g., the working electrode 408, the counter electrode 410, the reference electrode 412) may be less than about 1000 µm.

Figure 4B:
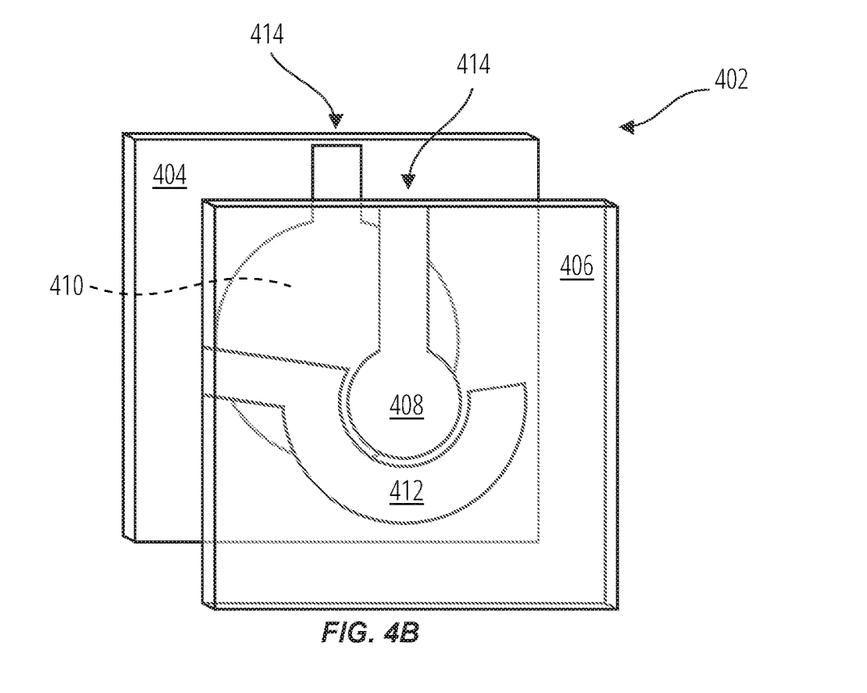
FIG. 4B is a perspective schematic illustration of the substrates and electrodes of the electrochemical sensor of FIG. 4A arranged in a spatial relationship for use within a harsh environment.

Prior to use, or at least prior to taking measurements with the electrochemical sensor 402, the first substrate 404 and the second substrate 406 may be positioned a predetermined distance from one another with the electrode-including surface of each directed toward one another. A separate support structure may be used to hold the first substrate 404 and the second substrate 406 in a fixed spatial relationship relative to one another. In other embodiments, the first substrate 404 and the second substrate 406 may be affixedly and physically connected to one another prior to use, and, in some such embodiments, prior to printing the electrodes (e.g., the working electrode 408, the counter electrode 410, the reference electrode 412) thereon. After printing the electrodes and before or after supporting the substrates in a desired relative position, electrical leads may be connected to the distal portion 414 of each of the electrodes (e.g., the working electrode 408, the counter electrode 410, the reference electrode 412) to electrically and operatively connect the electrochemical sensor 402 to a power source and or data-acquisition system.

Fabrication may also include, after forming the electrodes, additional material treatment and/or testing. Such additional testing may include inserting at least a portion of the electrochemical sensor within a harsh environment (e.g., a molten salt environment). Subsequent to such harsh environment insertion, the electrochemical sensors may be inspected to detect whether there has been any material adhesion, material degradation, or other structural defects. Other additional, or alternative, testing or treatments may include annealing and/or heat cycling, again with observations to determine whether there has been any material adhesion, material degradation, or other structural defects. Transient electrochemical measurements (e.g., cyclic voltammetry, open circuit potentiometry, chronopotentiometry, and/or impedance spectroscopy measurements) may also be performed on these electrodes to verify the operability and accuracy recorded by the electrochemical sensors.

The fabrication methods described above enable the control of the size, shape, and/or spatial relationship of the features (e.g., electrodes) of a sensor, such that sensors may be formed with intricate or complex designs, even at a small scale (e.g., in microsensors). Accordingly, sensors (e.g., microsensors) may be fabricated to tailor the sensor's measuring capabilities, sensitivities, and/or data accuracy according to the environment in which the sensors are to be deployed.

For example, conventional electrochemical sensors tend to have limited accuracy for certain measurements (e.g., voltage, current), particularly in harsh environments. These limitations may be the result of fabricating the sensors using conventional fabrication methods, which tend to not be conducive to forming electrochemical sensors at small (e.g., micro) sizes, with intricate electrode structures, with complex electrode geometries, with controlled electrode spatial relationships, and/or with unusual materials. Fabricated, conventional electrochemical sensors therefore often exhibit certain undesirable features that may limit the data measurability by the sensors, the accuracy of those measurements, and the means for analyzing the data. For example, conventional electrochemical sensors—which tend to be macroscale in size and without controlled, fixed electrode spatial relationships—used in molten salt environments generally take measurements that are at least somewhat limited by the diffusion characteristics of the electrochemically active species. Analyzing the data taken by such conventional sensors in molten salt environments tends to require the use of equations that account for the diffusion limitations. Such equations may therefore need to obey certain laws, e.g., Fick's law for mass transfer diffusion. On the other hand, by enabling fabrication of electrochemical sensors at small-scales (e.g., micro-scale), with intricate or complex electrode designs, with unique materials, and/or with controlled spatial relationships of electrodes, electrochemical sensors according to embodiments of the disclosure may be fabricated to avoid measurement sensitivities and/or with improved measurement accuracy, according to the system in which the sensor is to be used. Therefore, if a sensor is to be used in a molten salt environment that includes concentrations of electrochemically active species diffusing through a molten salt solution, the sensor may be fabricated to be at a size and of controlled electrode geometries and spatial relationships that the accuracy of the measurements (e.g., voltage, current) to be taken by the sensor are not negatively impacted by the diffusion characteristics of the electroactive species. Thus, data analysis need not necessarily be restricted to diffusion-sensitive equations. Instead, the sensors may be designed and fabricated to be reaction-limited, taking measurements that may be analyzed using equations based on reaction kinetics, rather than mass diffusion. Alternatively, the sensors may be designed and fabricated to be analyzed using equations based on mass transfer reactions. Therefore, the sensor design may be tailored according to the limitations of the system, the type of system (e.g., high-temperature, oxidizing, reducing, radioactive), the limitations of the measurements to be taken, and/or the limitations of the data analysis methods to be employed, rather than having to tailor the system or data analysis according to the limitations imposed by conventional sensors.

It is also contemplated that electrochemical sensors fabricated according to methods of the disclosure may enable data measurements, sensitivities, and/or data analysis that have conventionally not been possible or practically achievable, due to limitations on sensor design and fabrication.

Fabricating sensors, such as microsensors, by additive manufacturing through printing of conductive inks onto a surface of a substrate, may be carried out relatively quickly, compared to, e.g., conventional photolithography-based fabrication techniques. For example, in some embodiments, fabricating a sensor may not require substantial pre-printing treatment stages and/or substantial post-printing treatment stages (e.g., subsequent patterning stages (e.g., etching or other material-removal stages), annealing stages, coating-formation stages). In some embodiments, the sensors (e.g., the electrochemical sensor 200 of FIG. 2), the electrochemical sensor 302 of FIG. 3A and FIG. 3B, the electrochemical sensor 402 of FIG. 4A and FIG. 4B may be entirely free or substantially free of any additional coating or other material over the electrodes. That is, the printed, conductive material forming the electrodes (e.g., the working electrode 108, the counter electrode 110, the reference electrode 112 of FIG. 1; the working electrode 204, the counter electrode 206, the reference electrode 208 of FIG. 2; the working electrode 308, the counter electrode 310, the reference electrode 312 of FIG. 3A and FIG. 3B; the working electrode 408, the counter electrode 410, the reference electrode 412 of FIG. 4A and FIG. 4B) may be the outer-most material relative to the primary surface of the respective substrate (e.g., the substrate 106 of FIG. 1, the substrate 202 of FIG. 2; the first substrate 304 and the second substrate 306 of FIG. 3A and FIG. 3B; the first substrate 404 and the second substrate 406 of FIG. 4A and FIG. 4B).

The relative simplicity of the processes and equipment and the relative brevity of the process also leads to the fabrication methods being efficient and relatively inexpensive to perform. The relative speed with which a sensor may be fabricated also enables rapid prototyping. That is, a variety of sensor (e.g., microsensor) prototypes may be fabricated relatively quickly and then tested to evaluate the effectiveness of a variety of sensor designs and a variety of sensor materials (e.g., various ink (e.g., electrode) materials, such as metals, alloys, and/or conductive oxides; various substrate materials, such as semiconductor materials; etc.). Therefore, the methods described facilitate designing, fabricating, and testing a wide-range of sensor and electrode designs and materials.

While the disclosed methods, structures, apparatus (e.g., sensors), and systems are susceptible to various modifications and alternative forms in implementation thereof, specific embodiments have been shown by way of example in the drawings and have been described in detail herein. However, the disclosure is not intended to be limited to the particular forms disclosed. Rather, the disclosure encompasses all modifications, combinations, equivalents, variations, and alternatives falling within the scope of the disclosure as defined by the following appended claims and their legal equivalents.

What is claimed is:

1. A method for manufacturing an electrochemical sensor, comprising:
   forming at least one working electrode on at least one substrate, comprising printing at least one conductive ink on a surface of the at least one substrate, the at least one working electrode free of silver, gold, copper, silicon, and polymer materials and at least a portion of the at least one substrate, to be inserted into a molten salt environment during use of the electrochemical sensor, being free of silver, gold, copper, silicon, and polymer materials,
   forming at least one counter electrode on at least one substrate, comprising printing at least one other conductive ink on the surface or another surface of the at least one substrate, the at least one counter electrode free of silver, gold, copper, silicon, and polymer materials, and
   forming at least one reference electrode free of silver, gold, copper, silicon, and polymer materials on the at least one substrate.

2. The method of claim 1, wherein forming the at least one working electrode on the at least one substrate comprises printing all of the at least one working electrode of the electrochemical sensor on one of the at least one substrate.

3. The method of claim 1, wherein forming the at least one working electrode on the at least one substrate comprises printing the at least one conductive ink on a surface of at least one substrate comprising a ceramic material.

4. The method of claim 1, wherein forming the at least one working electrode on the at least one substrate comprises printing the at least one conductive ink on a surface of at least one substrate comprising one or more of a ceramic material, sapphire, or quartz.

5. The method of claim 1, wherein the printing comprises inkjet printing the at least one conductive ink on the surface of the at least one substrate.

6. The method of claim 1, wherein the printing comprises aerosol jet printing the at least one conductive ink on the surface of the at least one substrate.

7. The method of claim 1, further comprising, after forming the at least one working electrode on the at least one substrate, submerging at least a portion of the at least one working electrode and the at least one substrate within a molten salt.

8. The method of claim 1, wherein forming at least one working electrode on at least one substrate comprises printing the at least one conductive ink on the surface of the at least one substrate to form the at least one working electrode to have a width of less than about 100 μm.

9. An electrochemical sensor for use in a molten salt environment, the electrochemical sensor comprising:
   a working electrode on at least one substrate, the working electrode comprising a conductive material; and
   a counter electrode on the at least one substrate, the counter electrode comprising another conductive material,
   wherein:
      at least a portion of the electrochemical sensor, to be inserted into a molten salt environment during use of the electrochemical sensor, is free of silver, gold, copper, silicon, and polymer materials; and
      the electrochemical sensor further comprises a reference electrode on the at least one substrate.

10. The electrochemical sensor of claim 9, wherein reference electrode at least partially laterally circumscribes the working electrode.

11. The electrochemical sensor of claim 10, wherein:
   the working electrode and the reference electrode are disposed on a first substrate of the at least one substrate; and the counter electrode is disposed on a second substrate of the at least one substrate.

12. The electrochemical sensor of claim 9, wherein a greatest outer dimension of the electrochemical sensor is less than about 1000 µm.

13. The electrochemical sensor of claim 9, wherein the at least one substrate is substantially circular.

14. The electrochemical sensor of claim 9, wherein at least one of the conductive material or the other conductive material has a perovskite crystal structure.

15. The electrochemical sensor of claim 9, wherein the conductive material is not covered by another material.

16. An electrochemical sensor for use in a molten salt environment, the electrochemical sensor comprising:
   a working electrode on at least one substrate, the working electrode comprising a conductive material; and
   a counter electrode on the at least one substrate, the counter electrode comprising another conductive material,
   wherein at least a portion of the electrochemical sensor, to be inserted into a molten salt environment during use of the electrochemical sensor, is free of silver, gold, copper, silicon, and polymer materials; and
   wherein a greatest outer dimension of the electrochemical sensor is less than about 1000 µm.

17. The electrochemical sensor of claim 16, wherein the at least one substrate is free of silicon.

18. The electrochemical sensor of claim 16, wherein:
   the working electrode comprises a distal portion extending to an edge of the at least one substrate; and
   the counter electrode comprises another distal portion extending to the edge or another edge of the at least one substrate.

19. The electrochemical sensor of claim 16, wherein the conductive material and the other conductive material comprise one or more of:
   a transition-group metal with a melting point greater than about 400° C.;
   a conductive ceramic material;
   vitreous carbon; or
   a combination of any of the foregoing.

20. The electrochemical sensor of claim 16, wherein the at least one substrate comprises one or more of a ceramic material, sapphire, or quartz.

21. The electrochemical sensor of claim 16, wherein the working electrode and the counter electrode have a fixed position relative to one another.

* * * * *

UNITED STATES PATENT AND TRADEMARK OFFICE
CERTIFICATE OF CORRECTION

PATENT NO. : 11,635,404 B2
APPLICATION NO. : 16/840102
DATED : April 25, 2023
INVENTOR(S) : Michael R. Shaltry, Prabhat K. Tripathy and David Estrada It is certified that error appears in the above-identified patent and that said Letters Patent is hereby corrected as shown below:

In the Claims

| Claim 1, | Column 14, | Line 8, | change "on at least" to --on the at least-- |
| Claim 9, | Column 14, | Line 47, | change "Au electrochemical" to --An electrochemical-- |

Signed and Sealed this
Twenty-fifth Day of July, 2023

Katherine Kelly Vidal
*Director of the United States Patent and Trademark Office*